(12) United States Patent
Barone et al.

(10) Patent No.: US 11,565,270 B2
(45) Date of Patent: Jan. 31, 2023

(54) SYSTEM AND METHOD FOR CRYOGENIC SEPARATION OF PLANT MATERIAL

(71) Applicant: Cryocann USA Corporation, Santa Ana, CA (US)

(72) Inventors: Christopher Barone, Ranchos Palos Verdes, CA (US); Matt Armstrong, San Pedro, CA (US)

(73) Assignee: CRYOMASS LLC, Englewood, CO (US)

( * ) Notice: Subject to any disclaimer, the term of this patent is extended or adjusted under 35 U.S.C. 154(b) by 59 days.

(21) Appl. No.: 17/093,078

(22) Filed: Nov. 9, 2020

(65) Prior Publication Data

US 2021/0069725 A1 Mar. 11, 2021

Related U.S. Application Data

(62) Division of application No. 15/606,672, filed on May 26, 2017, now Pat. No. 10,864,525.

(51) Int. Cl.
| | |
|---|---|
| *B03B 1/00* | (2006.01) |
| *B03B 5/02* | (2006.01) |
| *A61K 36/185* | (2006.01) |
| *B03B 11/00* | (2006.01) |
| *B03B 5/58* | (2006.01) |

(52) U.S. Cl.
CPC .............. *B03B 1/00* (2013.01); *A61K 36/185* (2013.01); *B03B 5/02* (2013.01); *B03B 5/58* (2013.01); *B03B 11/00* (2013.01)

(58) Field of Classification Search
CPC .... B03B 1/00; B03B 5/02; B03B 5/58; B03B 11/00; A61K 36/185

USPC ............................................................ 209/3
See application file for complete search history.

(56) References Cited

U.S. PATENT DOCUMENTS

| | | | |
|---|---|---|---|
| 4,742,686 A | 5/1988 | Cook | |
| 8,640,877 B1 | 2/2014 | Pastorius | |
| 9,327,210 B1 | 5/2016 | Jones | |
| 10,857,482 B1 * | 12/2020 | Havens | B01D 11/0203 |
| 10,864,525 B1 * | 12/2020 | Barone | B03B 5/02 |
| 2004/0147769 A1 | 7/2004 | Davis | |
| 2011/0133120 A1 | 6/2011 | McGhee | |
| 2015/0360144 A1 | 12/2015 | Wasserman et al. | |
| 2017/0043276 A1 | 2/2017 | Tennant | |

(Continued)

FOREIGN PATENT DOCUMENTS

| | | | |
|---|---|---|---|
| EP | 2462941 A1 | 6/2012 | |
| EP | 3598969 A1 * | 1/2020 | A61K 31/352 |

(Continued)

*Primary Examiner* — Terrell H Matthews

(74) *Attorney, Agent, or Firm* — Carlson, Gaskey & Olds, P.C.

(57) ABSTRACT

Systems and methods for cryogenic separation of plant material are provided. A vessel is filled with cryogenic fluid having a temperature at or less than −150 degrees Celsius. Plant material is placed into the vessel via a basket and agitation is provided to the plant material in the vessel for a predetermined time period. Upon completion of the time period, the basket having at least a portion of the plant material is removed from the vessel. Plant particulates separated from the plant material during the agitation settle to the bottom of the vessel. The vessel is drained of the cryogenic fluid, including plant particulates separated from the plant material.

20 Claims, 3 Drawing Sheets

(56) References Cited

U.S. PATENT DOCUMENTS

| | | | |
|---|---|---|---|
| 2017/0231246 A1 | 8/2017 | Thompson | |
| 2017/0312651 A1 | 11/2017 | Galyuk | |
| 2017/0368022 A1* | 12/2017 | Sorbo | B01D 11/0273 |
| 2019/0328806 A1* | 10/2019 | Rapp | B01D 11/0207 |
| 2020/0086229 A1* | 3/2020 | Ko | A61K 36/185 |
| 2020/0188812 A1 | 6/2020 | Galyuk | |

FOREIGN PATENT DOCUMENTS

| | | |
|---|---|---|
| FR | 2997175 A1 | 4/2014 |
| WO | 2011057639 A1 | 5/2011 |
| WO | 2013092376 A1 | 6/2013 |
| WO | 2016092376 A1 | 6/2016 |

* cited by examiner

30

SYSTEM AND METHOD FOR CRYOGENIC SEPARATION OF PLANT MATERIAL

CROSS-REFERENCE TO RELATED APPLICATION

This application is a divisional of U.S. application Ser. No. 15/606,672, which was filed on May 26, 2017.

BACKGROUND

This application relates in general to separating plant particulates and, in particular, to a system and method for cryogenic separation of plant material.

Plant components are widely popular across different industries for use in cosmetics, perfumes, drug compositions, food, crafts, and fabrics. To obtain the necessary components, plant material must be processed to separate those components of the plant from other parts not needed. For instance, many pharmaceutical companies utilize pharmacologically active extracts that are separated from plant materials. However, separation processes must be carefully selected and performed to ensure purity and high yields of the desired component.

For example, indumentums of a plant often include the highest concentration of certain plant compounds, which are often used in drug manufacture. Indumentums are extremely fragile due to their resinous nature and can rupture during mechanical separation. Thus, much of the compounds can be lost due to rupture during conventional methods for extraction, such as solvent extractions and mechanical extractions.

Solvent separations require solvents, such as hydrocarbon, alcohol, or carbon dioxide, which can dissolve chemical components of a plant, such that indumentums are not physically preserved. The solvents eventually evaporate and only the chemical components are left together, without separation from other components.

Conventional processes for mechanical separation can be performed with or without an aqueous solution. Mechanical separation performed without an aqueous solution, such as water, utilizes a system of screens to separate plant components by size, but such process can cause the fragile indumentums to rupture. Mechanical separation can also require a matrix, such as water, which can alter the composition of the extracted plant component or a ratio of the desired plant components. Such process can include separation achieved through physical agitation in a reduced temperature aquatic matrix, followed by filtration through sequential layers of varied mesh, and finally drying of the separated plant component.

However, due to the aqueous nature of the separation, the minimum temperature for use in the extraction process is limited, which in turn limits the ability to preserve any volatile compounds. Also, preservation can be inhibited by retention of the plant components in the aqueous filtrate. Further, use of water as a solvent during the separation process and subsequent high moisture content of the plant particulates during and after separation can lead to waterborne pathogens, microbial growth, and other types of possible contamination.

Therefore, a need remains for a process that provides separated plant components, while maintaining a consistent chemical preservation of the desired components. Additionally, the process should be effective to result in high yields of the desired separated component, while ensuring that such components are sufficiently pure and free of contamination.

SUMMARY

Extraction of plant materials should be efficiently performed to prevent breakage or rupture of fragile components, such as indumentums, and ensure sufficiently pure components, free of contamination. Solvent extractions utilize solvents that dissolve chemical components of a plant, preventing preservations of certain components, such as indumentums, while most conventional mechanical extraction processes utilize aqueous solutions, which can lead to waterborne pathogens or microbial growth. Accordingly, a non-aqueous extraction process helps prevent any contamination due to water and includes filling a vessel with cryogenic fluid, placing one or more plants for processing into the vessel, providing agitation to the plants, and pulling the plant particulates remaining in the vessel out, while opening a valve in the vessel to release those components separated from the matrix.

One embodiment provides a system and method for cryogenic separation of plant material. A vessel is filled with cryogenic fluid having a temperature at or less than −150 degrees Celsius. Plant material is placed into the vessel via a basket and agitation is provided to the plant material in the vessel for a predetermined time period. Upon completion of the time period, the basket having at least a portion of the plant material is removed from the vessel. Plant particulates separated from the plant material during the agitation settle to the bottom of the vessel. The vessel is drained of the cryogenic fluid, including plant particulates separated from the plant material.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
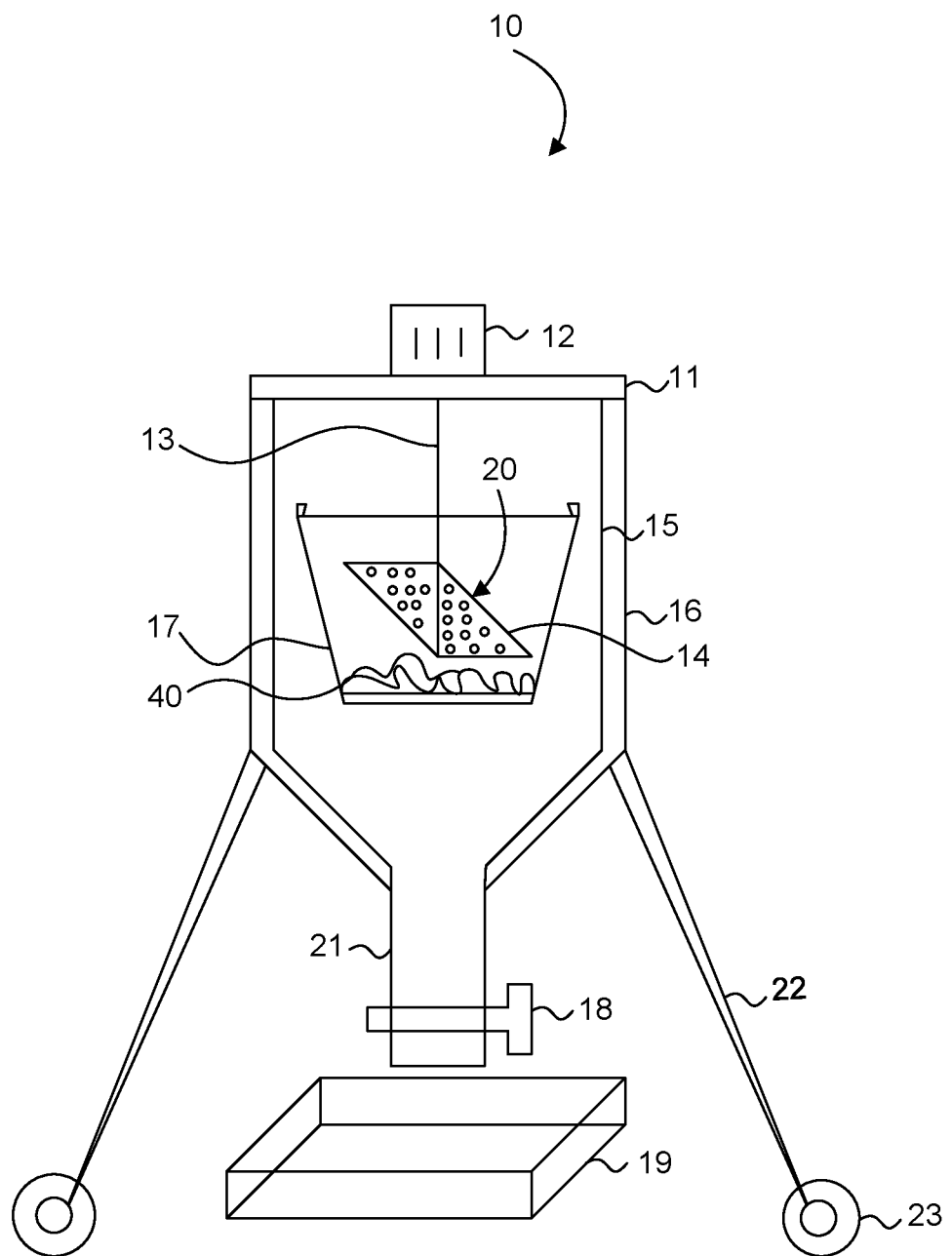
FIG. 1 is a side view of a separation system for separating plant material, in accordance with one embodiment.

Conventionally, some plant separation methods require the use of aqueous solutions. However, the use of such aqueous solutions can lead to contamination, such as waterborne pathogens and microbial growth. To prevent contamination from occurring, a non-aqueous separation process is utilized. FIG. 1 is a side view of a separation system 10 for separating plant material 40, in accordance with one embodiment. The separation system 10 includes a separation vessel 15, an agitator 20, at least one perforated basket 17, and a collection tray 19 to collect plant particulates separated from the plant material 40. Hereinafter, the terms "particulate" and "component" are used interchangeably with the same intended meaning, unless otherwise indicated.

The separation vessel 15 can have a conical shape with an opening on a top end that extends through a bottom end, which tapers into a stem 21 with a valve 18 to regulate the flow of fluid through the vessel. The vessel 15 can be made from material, such as food grade stainless steel, as well as other types of material. At a minimum, the material should be able to withstand extended contact with cryogenic fluids, such as those fluids with a temperature of −150 degrees Celsius or less.

The vessel 15 can be supported and raised via three or more support legs 22. The length and number of the legs 22 can be dependent on the size of the vessel 15 and placement of the vessel 15. For example, when the vessel 15 is sized to be placed on a table, the legs 22 will likely be shorter than when the vessel 15 is larger and must be placed on the floor. Additionally, as the vessel size increases, the size and number of the legs 22 can also increase. Each of the legs 22 can have a shape, such as conical or square, and include a rolling caster 23 with a lock to allow easy movement of the vessel. Other shapes of the vessel and legs are possible.

In one embodiment, a jacket 16 can be placed over at least a portion of the vessel 15 to control a temperature inside the vessel 15 and prevent excessive condensation on the surface of the vessel. The vessel jacket 16 can be filled with an insulator, such as foam or voided with a vacuum. In one embodiment, the vacuum can range from 759 torr down to a minimum pressure rating assigned to the vessel. For example, a stainless steel vessel has a lower minimum pressure rating than a vessel made from food grade polymeric material.

Figure 3:
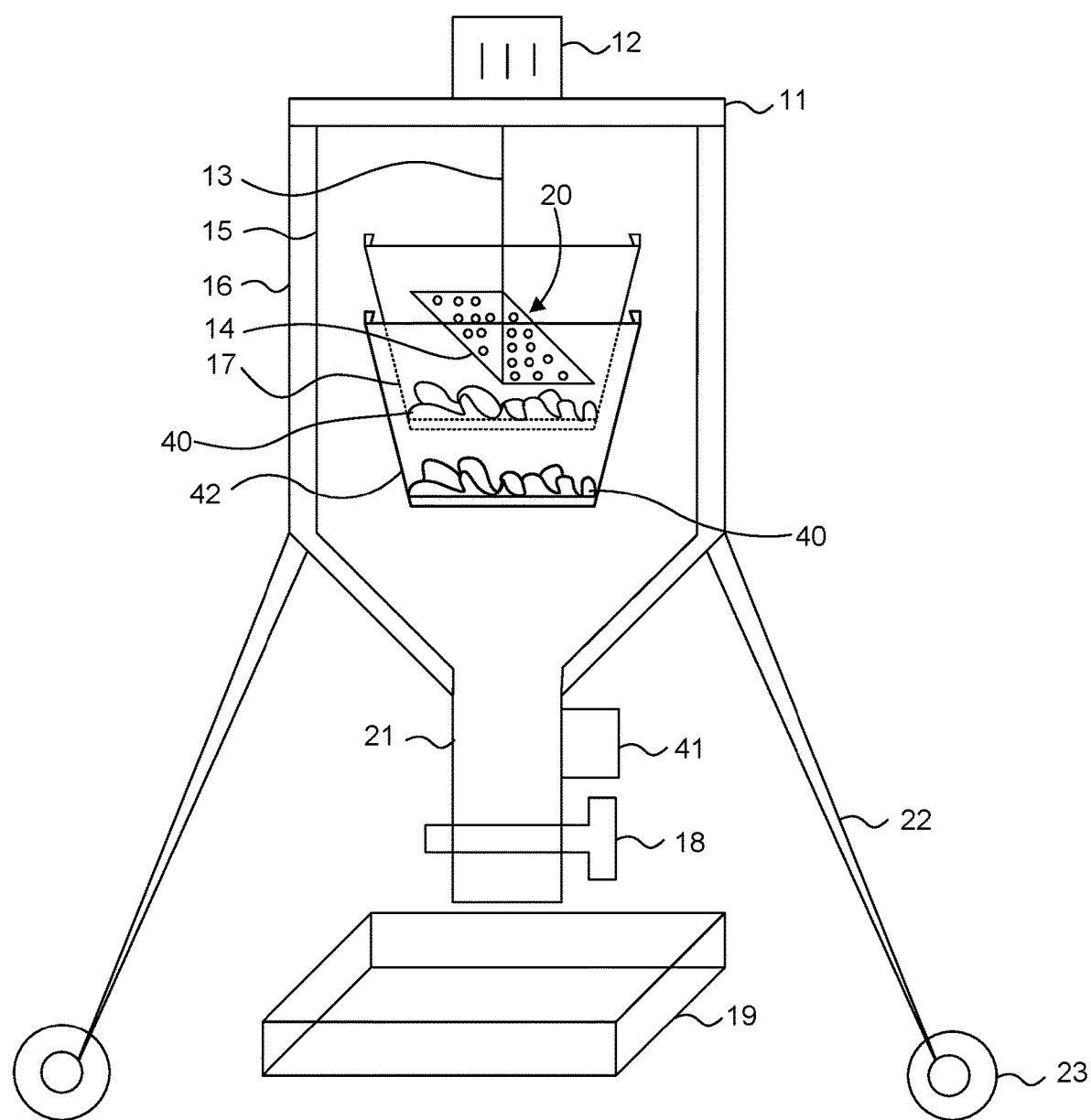
FIG. 3 is a side view of a different separation system for separating plant material, in accordance with one embodiment.

One or more baskets 17 can be used within the vessel 15 by placing the baskets 17 through the opening. FIG. 3 is a side view of the separation system of FIG. 1 with an additional basket, in accordance with on embodiment. When multiple baskets are used, the baskets 17, 42 can be nested together within the vessel 15 to increase a selectivity of the separation that will occur. The different baskets may have different diameters of mesh as to isolate plant particulates of varying size. For example, the more baskets used, the more likely the desired component is, by itself, separated from the remaining plant material. Each basket 17 can be made from a mesh material, such as stainless steel, with a diameter of open space, between grids of the mesh material, between 10-10,000 microns. The diameter of the mesh material and the number of baskets used can be based on the desired plant material to be processed or the desired plant component to be separated, as well as a desired level of separation. Additionally, a width of the mesh grids can be in the range of 25-400 um; however, in one embodiment a size of 305 um is used. Other sizes of the mesh diameter and grid width are possible, as well as other types of mesh material. At a minimum, the material for the basket 17 should be able to withstand temperatures at or below −150 degrees Celsius. A shape of the baskets can be tapered on a bottom end and include at least one handle or attachment point for use during insertion and removal of the basket from the vessel.

Figure 2:
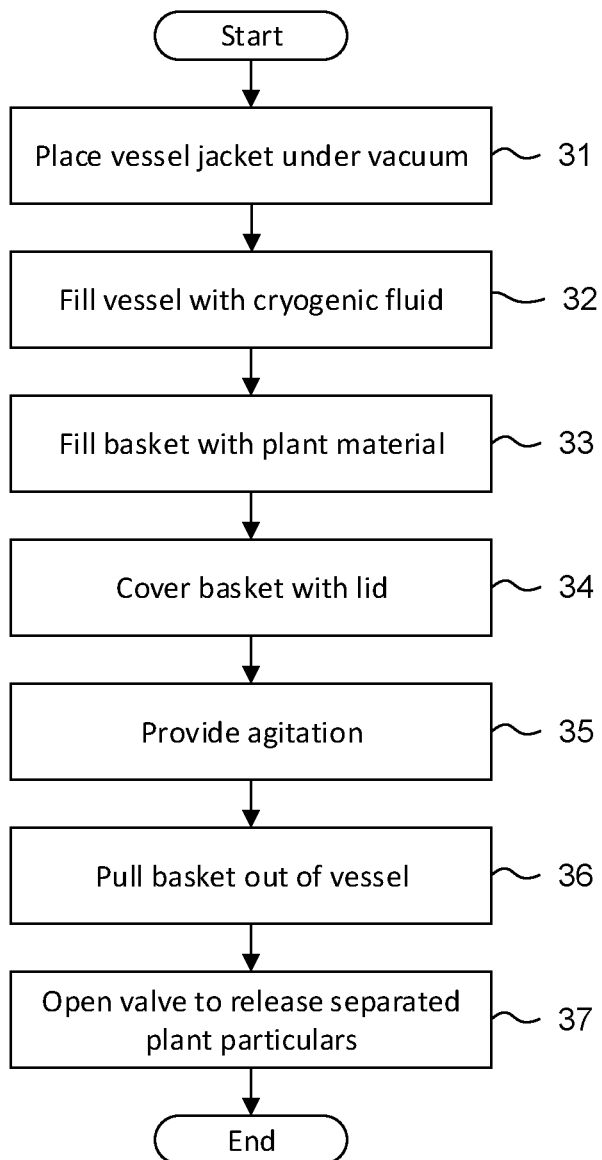
FIG. 2 is a flow diagram showing a method for separating plant material using the separation system of FIG. 1.

Returning to the discussion with reference to FIG. 2, during the separation process, a lid 11 can be placed over the top opening of the vessel 15. The agitator 20 can be affixed to the bottom side of the lid 11, facing inside of the vessel, and can be powered manually or via a motor 12, which can be affixed to a top side of the lid 11. The agitator 20 can include a shaft 13 that extends from the bottom side of the lid and extends downward. One or more paddles 14 are affixed on one end of the shaft 13, opposite the lid 11. The paddles 14 are each shaped as one of a rectangle, square, triangle, oval, or trapezoid, however, other paddle shapes are possible. The paddles 14 can have the same shape and size, or different shapes and sizes. Additionally, in one embodiment, one or more of the paddles can be perforated with holes of varying circumference.

A length of the agitator shaft 13 is dependent on a depth of the vessel 15 and any baskets 17 placed into the vessel. Additionally, the paddle shape and size is dependent on a diameter of the inside of the vessel. At a minimum, the paddles 14 should conformably fit within the vessel and any baskets 17 placed within the vessel. Preferably, the paddles extend from the shaft to a point just short of an inside wall of the basket to prevent obstruction of the paddles during agitation.

The agitator facilitates separation of plant material placed into the vessel. FIG. 2 is a flow diagram showing a method for separating plant material via the separation system of FIG. 1. The jacket surrounding at least a portion of the vessel is either filled with an insulator or voided with a vacuum. In one embodiment, the jacket is placed (block 31) under a vacuum in the range of 759 torr down to the minimum pressure rating of the vessel. Next, upon ensuring the valve is in a closed position, the vessel is filled (block 32) with cryogenic fluid to a predefined mark. In one embodiment, the fill mark can be determined to prevent spilling of the cryogenic fluid out of the vessel due to displacement by a basket and plant material.

The cryogenic fluid can include helium, hydrogen, nitrogen, neon, air, oxygen, fluorine, argon, methane, or a combination of such fluids. Additionally, other types of cryogenic fluids are possible. At a minimum, the cryogenic fluid should be at or below −150 degrees Celsius. In one embodiment, liquid nitrogen is used.

Plant material is placed (block 33) in at least one basket that is lowered (block 34) into the cryogenic fluid though the opening in the vessel. The plant material can include whole plants, flowers, trimmings, leaves, stalks, roots, or stems, as well as any other plant parts. An amount of the plant material to be placed in the vessel is dependent on a size of the vessel. In one embodiment, up to 3,000 grams of plant material can be processed at a single time; however, other amounts are possible. Prior to placement in the basket, the plant material is frozen and subsequently pulverized. In one embodiment, the plant material is recently harvested to prevent drying of the plant and maximize preservation of desired plant components and other chemical compounds within the plant material.

Once the basket is positioned in the vessel, the lid is placed on the vessel and the agitator provides (block 35) agitation to the plant material by spinning the paddles within the basket, which results in separation of particular components from the plant material. The agitation can occur manually or via a motor. The environment inside the vessel, provided by the cryogenic liquid, helps solidify certain plant particulates, such as indumentums, and makes those particulates easily separable from the plant material, such as by reducing rupture due to the agitation and force of separation. Additional baskets with varying sizes of mesh can be used to separate different plant components by size.

The agitation should be performed for a time period long enough to sufficiently separate a desired component, such as between one and 60 minutes, and at a speed fast enough to ensure full agitation of the plant material within the cryogenic fluid. In one embodiment, the agitation time should be between 10 and 15 minutes.

Upon completion of the agitation, the lid is removed and the basket, with any remaining plant material, is raised (block 36) above the cryogenic fluid for draining. The plant particulates can be allowed to settle to the bottom of the vessel, in or near the tapered stem area above the valve, over the course of 1-30 minutes. However, other times are possible, such as over 30 minutes. The valve is then moved (block 37) to an open position to allow the separated plant particulate to exit the vessel onto the collection tray via the cryogenic fluid. In one embodiment, the valve can be toggled between open and close positions to release a minimum volume of cryogenic fluid to fully empty the separated plant particulate. Once clean fluid flows, the valve is closed. The separated plant particulate, upon removal from the vessel, can have a water content up to 90% and can be dried to a desired concentration using, for example, a freeze dryer. However, other drying methods are possible.

An amount of drying can be based on the separated plant particulate. In one embodiment, drying should occur until the plant particulate has a moisture content of less than 10%. Additionally, refinement of the separated plant particulate can be performed prior to or after drying. Refinement can occur via by passing the separated plant particulate though additional sieves or screens to isolate target plant components, performing a solvent extraction of the separated plant particulate, steaming the plant particulate, or performing a vacuum distillation. The separation process can be repeated using the same cryogenic fluid with new plant material.

Once separations have been completed, the vessel and all other parts should be cleaned. Due to the vessel design, cleaning is easily performed and can reduce the time necessary between the separation of different plant materials, which increases the amount of plant material processed during a particular time period. Also, the lack of pumps and tubing, as well as the lack of water, helps prevent the introduction of microbial contamination.

In one example, cannabis has thermolabile compounds, which are most highly concentrated in the indumentums of the cannabis plant. As part of the separation process, the cannabis plants are frozen, pulverized, and placed in a basket with a mesh grid having a size of 305 um. The basket and cannabis plants are lowered into the cryogenic fluid. For instance, 3,000 g of cannabis can be processed at a time. Manual agitation can be performed for 12 minutes, after which the basket is removed from the cryogenic fluid and drained. The valve is released and the indumentums, which were separated from the cannabis plant during agitation, are released from the vessel. The indumentums are then placed in a freeze dryer for 18 hours.

In a further embodiment, a recirculating pump 41, as shown in FIG. 3, can be installed on a bottom of the vessel. The recirculating pump 41 can pump liquid from the bottom of the vessel to the top of the vessel, such as to a predefined mark or liquid line inside the vessel. Recirculating the liquid in the vessel creates a circular downward flow, which facilitates filtration.

While the invention has been particularly shown and described as referenced to the embodiments thereof, those skilled in the art will understand that the foregoing and other changes in form and detail may be made therein without departing from the spirit and scope.

What is claimed is:

1. A method of cryogenic separation of plant material, the method comprising:
    a) providing cryogenic fluid at or below −150 degrees Celsius within a vessel;
    b) placing a container into the cryogenic fluid in the vessel;
    c) placing plant material into the container;
    d) agitating the plant material within the container and the vessel to separate plant particulates solidified by the cryogenic fluid from the remainder of the plant material; and
    e) draining the cryogenic fluid and plant particulates from the vessel.

2. The method as recited in claim 1, wherein the container includes a mesh material.

3. The method as recited in claim 2, wherein the container is a basket.

4. The method as recited in claim 3, wherein step (e) comprises opening a valve.

5. The method as recited in claim 1, wherein step (e) comprises opening a valve.

6. The method as recited in claim 1, wherein step (d) is performed by an agitator comprising a shaft and at least one paddle at an end of the shaft.

7. The method as recited in claim 6, wherein step (d) includes spinning the at least one paddle within the container.

8. The method as recited in claim 1, wherein the cryogenic fluid comprises liquid nitrogen.

9. The method as recited in claim 1, the method comprising:
    before step (e), allowing the plant particulates to settle at a bottom portion of the vessel.

10. The method as recited in claim 9, wherein the bottom portion includes a tapered stem area.

11. The method as recited in claim 1, wherein step (c) is performed before step (b).

12. The method as recited in claim 11, the method comprising:
    placing a jacket around at least a portion of the vessel; and
    performing at least one of:
    filling the jacket with an insulator; and
    voiding the jacket with a vacuum.

13. The method as recited in claim 1, the method comprising:
    pulverizing the plant material prior to placement in the vessel; and
    freezing the plant material prior to placement in the vessel.

14. A method of cryogenic separation of plant material, the method comprising:
    a) providing cryogenic fluid at or below −150 degrees Celsius within a vessel, the cryogenic fluid comprising liquid nitrogen;
    b) placing a mesh container into the cryogenic fluid in the vessel;
    c) placing plant material into the container;
    d) agitating the plant material within the container and the vessel to separate plant particulates solidified by the cryogenic fluid from the remainder of the plant material;
    e) allowing the plant particulates to settle at a bottom portion of the vessel; and
    f) draining the cryogenic fluid and plant particulates from the vessel.

15. The method as recited in claim 14, wherein step (d) is performed by an agitator comprising a shaft and at least one paddle at an end of the shaft.

16. The method as recited in claim 15, wherein step (d) includes spinning the at least one paddle within the container.

17. The method as recited in claim 16, wherein step (f) comprises opening a valve.

18. The method as recited in claim 14, wherein step (f) comprises opening a valve.

19. The method as recited in claim 18, wherein the container is a basket.

20. The method as recited in claim 19, wherein the bottom portion includes a tapered stem area.

\* \* \* \* \*